United States Patent [19]

Yamamoto et al.

[11] Patent Number: 5,212,076
[45] Date of Patent: May 18, 1993

[54] PRODUCTION OF QUERCETIN GLUCURONIDE

[75] Inventors: Yoshikazu Yamamoto; Yasuhiro Kinoshita, both of Neyagawa, Japan

[73] Assignee: Nippon Paint Co., Ltd., Osaka, Japan

[21] Appl. No.: 760,352

[22] Filed: Sep. 16, 1991

[30] Foreign Application Priority Data

Sep. 17, 1990 [JP] Japan .................................. 2-248457

[51] Int. Cl.$^5$ .................. C12R 1/91; C12P 19/60; C07H 17/07
[52] U.S. Cl. .................. 435/75; 435/74; 435/240.48; 435/948; 536/4.1; 536/8
[58] Field of Search .................. 435/74, 75, 240.48, 435/240.49, 948; 536/4.1, 8

[56] References Cited

U.S. PATENT DOCUMENTS 4,338,399  6/1982  Weil et al. ........................... 435/267
4,363,188  12/1982  Lovelace et al. ............... 435/240.49

OTHER PUBLICATIONS

Derwent Abs 92-196053/24 (Abstract JP04119180 Apr. 1990) Nippon Paint Co.

Primary Examiner—Herbert J. Lilling
Attorney, Agent, or Firm—Wenderoth, Lind & Ponack

[57] ABSTRACT

The present invention provides a dye other than red and purple which is obtained from cultured cells of *Euphorbia milli*. The present invention also provides cultured cells containing quercetin glucuronide in a large amount, derived from tissues or cells of *Euphorbia milli*.

1 Claim, 2 Drawing Sheets

PRODUCTION OF QUERCETIN GLUCURONIDE

FIELD OF THE INVENTION

The present invention relates to a process for preparing quercetin glucuronide obtained from cultured cells derived from plant tissues and cells of *Euphorbia milli*.

BACKGROUND OF THE INVENTION

A dye is generally formulated in food as a food colorant to make it clear or vivid, but synthetic colorants are restrictively used because of toxicity (e.g. mutability). A colorant which is derived from natural materials, especially natural plants, is therefore much desired in practical use in view of safety.

However, the growth of the natural plants is dependent on surrounding conditions, such as season, climate, temperature, latitude, land shape, water transportation, soil and the like, the colorants derived from the natural plants are not constantly and stably supplied. A large cultivation using arable land contends with food production and therefore the supply of the natural plants has a limit. Also, as mentioned above, the productivity of the plants has a limit which makes cost-up.

On the other hand, plant cell culture has been intensely studied as means for producing plants. The plant cell culture can produce desired components in a very short period of time in comparison with the natural culture in which plants grow in years or months. Also, the plant cell culture is not affected by natural conditions, such as weather and can intentionally produce them in an industrial scale. The labor for the cultivation is also lowered.

The present inventors proposed that a red natural dye was obtained from callus tissues derived from plant tissues of *Euphorbia milli* which had been cultured on a culture medium containing 2,4-D as a plant hormone. It was also proposed that the callus tissues were cultured on a culture medium containing alpha-naphthalenacetic acid (NAA) to produce a red natural dye. Further, a purple dye derived from *Euphorbia milli* was also proposed (See Japanese Kokai Publications 57-222695, 57-2697 and 63-24-795).

SUMMARY OF THE INVENTION

The present inventors have studied that a dye other than red and purple is obtained from the cultured cells of *Euphorbia milli*. The present invention provides quercetin glucuronide which is one of yellow dye and obtained by extracting from cultured cells derived from tissues or cells of *Euphorbia milli*.

The present invention also provides cultured cells containing quercetin glucuronide in a large amount, derived from tissues or cells of *Euphorbia milli*.

DETAILED DESCRIPTION OF THE INVENTION

Quercetin glucuronide of the present invention is a quercetin glucoside having the following chemical formula;

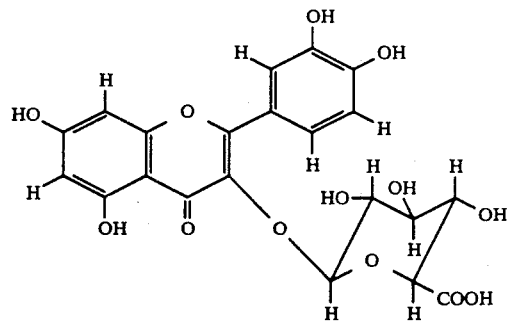

The plant cultured cells employed in the present invention are derived from *Euphorbia milli*.

The portion to be cultured of the plant is all tissues of *Euphorbia milli*. A division tissue and a node tissue can be used, but the latter is preferred because of high propagation rate of the culture cell or culture tissue derived therefrom. By "division tissue" is meant a tissue contributing to growth of plants by way of cell division in the tissue of plants. Preferred are a terminal bud and a lateral bud. By "node tissue" is meant a portion of stalk to which a leaf is attached or being attached, which is contrasted to a tissue between nodes.

The cultured plant cells are plant cells derived from the tissue or cell of plants and artificially cultured in a container. The cultured plant cells include callus tissues, differentiated cultured tissues, cultured organ tissues and the like. The callus tissues (hereinafter simply referred to "callus") are cultured plant cells lump only consisting of shapeless undifferentiated cells propagated over solid culture medium containing plant hormones or in liquid culture medium containing the plant hormones. The differentiated tissues are cultured plant cells lump composed of tissue having been differentiated (such as a root, a bud or a shoot) and undifferentiated cells. It includes adventive buds (consisting of bud tissues and undifferentiated cells), adventive roots (consisting of root tissues and undifferentiated cells) and cormus cultivated tissues (consisting of shoot tissues and undifferentiated cells). The cultured organs are cultured plant cells lump solely consisting of differentiated tissues which include cultured roots, cultured shoot and the like.

A method for culturing cells of *Euphorbia milli* is illustrated.

Leaves of *Euphorbia milli* are washed with deionized water and various germs on the surface of them are removed by immersing in a 70% ethanol for 5 to 10 minutes and then in a bleaching powder solution for 5 to 10 minutes, followed by removing a remaining sterilizing agent with a sterilized distilled water. The sterilized leaves are cut with a sterilizing knife to portions having a suitable size. The cut portions are placed on a synthetic culture medium containing an auxine, such as 2,4-dichlorophenoxyacetic acid (2,4-D), alpha-naphthaleneacetic acid (NAA) and the like, (e.g. Murashige skoog culture medium).

Thereafter, the culture medium was cultured at a temperature of 20° to 30° C., preferably about 28° C., in a bright place, preferable having more than 100 1×, preferably 3,000 to 100,000 1×. After one week, callus tissues are formed from the portions of the leaves. The callus is then placed on a new agar culture medium and cultured at a temperature of 20° to 30° C., preferably about 28° C., in a bright place, preferable having more than 100 1×, preferably 3,000 to 100,000 1×. In case where cultured cells are obtained in an industrial scale, the callus is cultured and propagated by the same operation as culture methods of microorganisms, such as a stand culture method or a liquid culture method. The liquid culture method can be either a shaking culture method wherein culture is conducted on a shaking culture machine, or an air blowing method wherein sterilized air is passed through a closed glass or metal container.

The culture medium for culturing the plant tissue is known to the art and generally inorganic synthetic agar culture mediums which are added with a trace amount of organic materials (e.g. vitamines), carbon sources, plant hormones and various natural extracts.

The organic materials include vitamines, such as tiamine hydrochloride, pyridoxine hydrochloride, nicotinic acid and the like; amino acids, such as glycine, asparagine and the like; and heptahydric alcohols, such as inositol, sorbitol and the like. The culture medium without these organic material can be used and may often propagate plant cells satisfactorily.

The carbon sources include carbohydrates, such as sucrose, glucose, maltose and the like; organic acids, such as acetic acid and the like; alcohols, such as methanol, glycerol and the like.

Examples of the plant hormones are auxines, such as 2,4-dichlorophenoxyacetic acid (2,4-D), beta-indoleacetic acid (IAA) and alpha-naphthaleneacetic acid (NAA); cytokinins, such as kinetin; and the like.

Examples of the natural extracts are casein hydrolysate (0 to 2% w/v), coconuts milk (0 to 25% w/v), yeast extracts (0 to 2% w/v), malt extracts (0 to 2% w/v), a mixture thereof and the like.

The cultured cells are obtain as mentioned above, but those which contain quercetin glucuronide in a large amount are obtained by repeating the following steps (a) to (c) (See Japanese Kokai Publication 57-16692): (a) A cultured cell lump is sterilely divided into small lumps having a size of 2 to 10 mm. (b) The small lumps are cultured and propagated on a culture medium; (c) Among the cultured lumps, some yellowish lumps are selected.

The cultured cells which contains a large amount of quercetin glucuronide are subjected to extraction with a neutral solvent. Typical examples of the neutral solvents are alcohols, such as butanol, ethanol, methanol and a mixture thereof. Preferred alcohols are lower alcohols. In the conventional extractions of the cultured cells, acid (such as hydrochloric acid, acetic acid and formic acid) is added to the solvent, but in the present invention such acid is not added. The cultured cells are generally freeze-dried and then immersed in the neutral solvent to extract. The extracted solution is generally filtered to remove the solid content and then evaporated at 40° C. or less. The resultant concentrated extract is mixed with water and then rinsed several times with an ether. It is extracted with an organic solvent which is separable with water, such as butanol, to obtain quercetin glucuronide which may be purified by a known method, such as thin layer chromatography, liquid chromatography and the like.

According to present invention, quercetin glucuronide is obtained by extracting the cultured plant cells with a neutral solvent. The quercetin glucuronide has yellow color and is the same as yellow color dyes which are naturally obtainable. The quercetin glucuronide is employed as yellow dye, but also has ultraviolet absorbing ability, thus useful for a dye of foods, cosmetics and the like.

EXAMPLES

The present invention is illustrated by the following Examples which are not to be construed as limiting the present invention.

EXAMPLE 1

Leaves of *Euphorbia milli* were washed with water and cut to a size of 4 cm$^2$. The cut sections were immersed in a 70% ethanol for 5 minutes and then in a 10% bleaching powder solution for 10 minutes to sterilize. They were further immersed in sterilized distilled water for several times to remove the remaining sterilizing agent. The sterilized sections were further cut to size of 1 cm$^2$ with a sterilized knife. The sterilized sections were placed on a synthetic agar culture medium having the following composition. To an inorganic salt culture medium of Murashige-skoog, 3% w/v of sucrose, 0.2% w/v of a malt extract, $10^{-6}$ M 2,4-D, 0.1 ppm of tiamine hydrochloride, 0.5 ppm of pyridoxine hydrochloride, 0.5 ppm of nicotinic acid, 2 ppm of glycine and 100 ppm of inositol were added and adjusted to pH 6.0. It was then mixed with 0.8 % w/v of agar and sterilized.

The segments placed on the culture medium were cultured at a culture temperature of 25° C. under the light of 3,000 1×. After three weeks, callus was developed from the segments. The propagated callus was divided to small segments after one month and some yellow lumps were selected therefrom. The yellow lumps were transferred onto another culture medium having the same composition as mentioned above and culturing continued at 25° C. under 3,000 1×. The same operations were repeated every 4 to 6 weeks and for total 6 months.

The cultured cells of *Euphorbia milli are* taken from the solid culture medium and dried in a vacuum freeze-drying machine to obtain dried callus of 10 g. The callus was ground by a mortar and immersed in methanol for 24 hours. The methanol extract was concentrated to about 50 ml at 40° C. or less and then charged in a separating funnel, to which 100 ml of ether was added and shaken, and the ether layer was removed. The ether extraction operations were repeated several times and then concentrated to 5 or 6 ml at 40° C. or less under reduced pressure. To the concentrated solution, 100 ml of water was added and the 100 ml of butanol added, which was charged in a separating funnel. After shaking, the butanol layer was recovered. The butanol extraction operations were also repeated several times. The butanol extract was concentrated at 40° C. or less and dried. The dried material was purified by cellulose thin layer chromatography using a developer (butanol-/acetic acid/water=4/1/5) to obtain 37 mg of quercetin glucuronide. The obtained quercetin glucuronide was subjected to UV spectrum and $^1$H-NMR which are shown in FIGS. 1 and 2.

Figure 1:
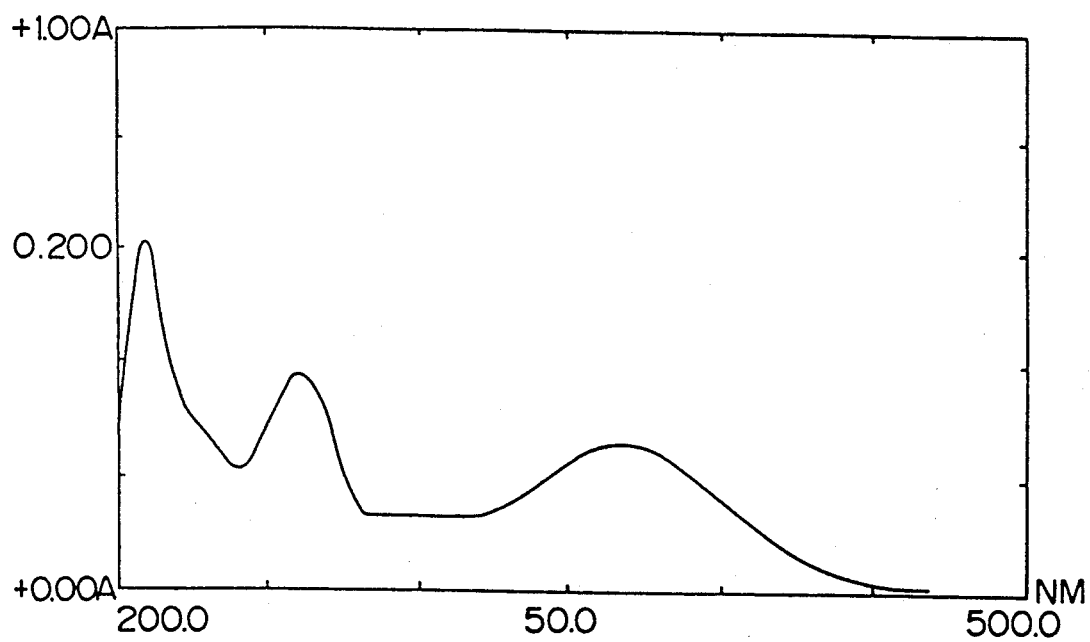
FIG. 1 shows a UV spectrum of a 0.05% methanol solution of quercetin glucuronide obtained in Example 1.
Figure 2:
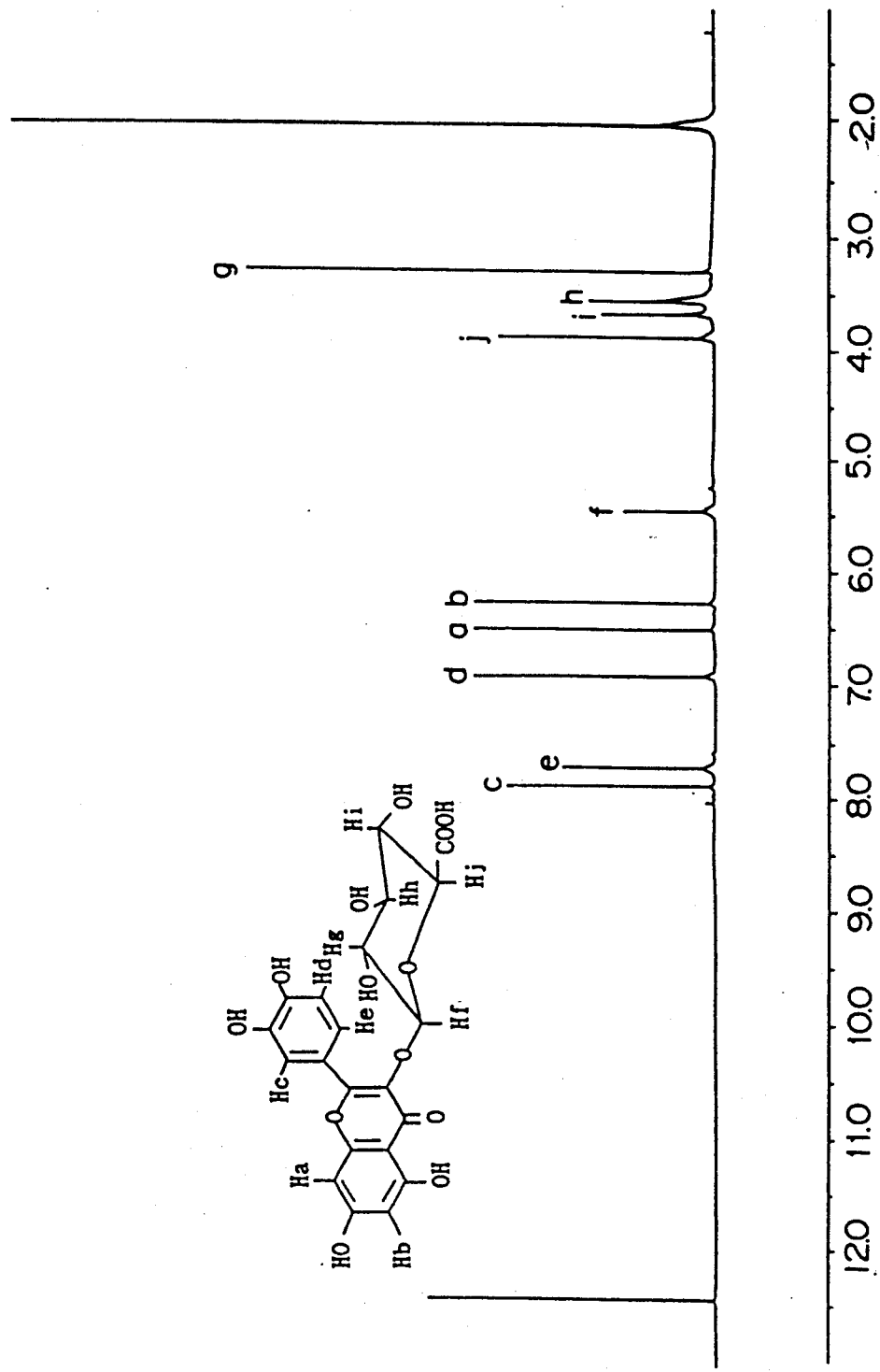
FIG. 2 shows a $^1$H-NMR spectrum of a D6 acetone solution of quercetin glucuronide obtained in Example 1.

What is claimed is:

1. A process for producing quercetin glucuronide comprising;

culturing tissues or cells of *Euphorbia milli* to form callus, dividing the callus to small lumps, selecting yellowing lumps, repeating the above steps, and collecting yellowish cultured cells and extracting with a neutral organic solvent.